United States Patent [19]

Carter et al.

[11] Patent Number: 4,996,152

[45] Date of Patent: Feb. 26, 1991

[54] AVIAN HERPESVIRUS AMPLICON AS A EUCARYOTIC EXPRESSION VECTOR

[75] Inventors: Jeanne K. Carter, Cincinnati, Ohio; Robert F. Silva, Okemos, Mich.

[73] Assignee: The United States of America, as represented by the Secretary of Agriculture, Washington, D.C.

[21] Appl. No.: 128,836

[22] Filed: Dec. 4, 1987

[51] Int. Cl.$^5$ .............................................. C12N 15/03
[52] U.S. Cl. .............................. 435/172.3; 435/172.1; 435/235.1; 435/237; 435/320.1; 536/27
[58] Field of Search .............. 435/235, 237, 68, 172.1, 435/172.3, 320, 69.1; 536/27; 935/27, 32, 57, 70

[56] References Cited

PUBLICATIONS

Silva and Witter (1985), Genomic Expansion of MDV, etc., J. Virol. 54 (3), 690–696.
Maotani et al. (1986), Amplification of a TDR etc., J. Virol. 58 (2) 657–660.
Kwong and Frenkel (1985), HSV Amplicon-IV Efficient Expression, etc., Virology 142 421–5.
Frenkel (1981), Defective Interfering Herpesviruses, Chapter in Human Herpesviruses Ed. by Nahmias et al., Elsevier, 1981 pp. 91–120.
Spaete et al. (1985), HSV Amplicon: Analysis etc., P.N.A.S. 82 694–8.
Yates et al. (1985), Stable Replication of etc., Nature 313 812–815.
Spaeke and Mocarski (1985), "A" Sequence of Cytomegalovirus, etc., J. Virology 54 (3), 817–824.
Spaeke and Frenkel (1982), HSV Amplicon: A New . . . Vector, Cell 30 295–304.
R. R. Spaete et al., "The Herpes Simplex Virus Amplicon: A New Eucaryotic Defective-Virus Cloning-Amplifying Vector," Cell 30: 295–304 (Aug. 1982).
A. D. Kwong et al., "Herpes Simplex Virus Amplicon: Effect of Size on Replication of Constructed Defective Genomes Containing Eucaryotic DNA Sequences," J. Virol. 51 (3): 595–603 (Sep. 1984).
A. D. Kwong et al., "The Herpes Simplex Virus Amplicon. IV. Efficient Expression of a Chimeric Chicken Ovalbumin Gene Amplified Within Defective Virus Genomes," Virology 142: 421–425 (1985).

Primary Examiner—Richard A. Schwartz
Attorney, Agent, or Firm—M. Howard Silverstein; Curtis P. Ribando; John D. Fado

[57] ABSTRACT

DNA fragments (seeds) having the characteristics of amplicons, which are useful for amplifying genes of interest, have been isolated from Marek's disease viruses of poultry. Concatmers of the seeds and the associated genes have potential as vaccines or delivery vectors when cotransfected and replicated in the presence of helper viruses. The amplicons are also useful for inserting associated genes into the helper viruses, which in turn could be used as expression vectors. Candidate genes for use with the subject amplicons include those which encode immunogenic proteins and other beneficial economic traits desired in commercial poultry lines.

12 Claims, 1 Drawing Sheet

AVIAN HERPESVIRUS AMPLICON AS A EUCARYOTIC EXPRESSION VECTOR

BACKGROUND OF THE INVENTION

1. Field of the Invention

This invention relates to the construction of a genetically engineered vector which would be useful as a vaccine against poultry diseases or for ferrying desirable genes into the avian system. There are over 4 billion chickens and 200 million turkeys raised annually in the United States alone. On the average, each bird is vaccinated against 10 different diseases. There are several problems associated with conventional vaccines in current use against poultry diseases. Killed or subunit vaccines, which are necessary for some pathogens, are safe but relatively inefficient. The live vaccines are typically more effective, but occasionally exhibit undesirable pathogenic effects. Another problem with current poultry vaccines is that they are susceptible to vaccine breaks; that is, the current vaccines do not provide protection against new, highly virulent strains of pathogens. Finally, some pathogens such as avian influenza have no existing vaccine, and the pathogenic nature of the infectious agent has precluded the development of either a live or killed virus vaccine.

In light of the problems with conventional vaccines, there are some obvious advantages of developing a genetically engineered vector which would be useful as a vaccine. Such a vector could be constructed which lacked or contained only a portion of any viral genes responsible for pathogenesis. This would enable protection without the risk of disease induction. In addition, polyvalent, live recombinant DNA vaccines expressing several different foreign genes could be easily constructed. These should be less expensive to prepare and administer than multiple current subunit or attenuated vaccines. Most importantly, rDNA vaccines could be constructed that are more efficacious than existing vaccines. By using the proper promoters, a live rDNA vaccine could be induced to express a higher level of immunogenic proteins than could be obtained with conventional attenuated vaccines, thereby more strongly stimulating a protective response in the host immune system. Live rDNA vaccines will stimulate both humoral and cell mediated immunity, unlike subunit vaccines that only stimulate humoral immunity.

Some of the avian herpesviruses, particularly Marek's disease virus (MDV), are the cause of economically important diseases in poultry. As a result of the economic attention given to MDV, it has been the subject of extensive scientific investigation in recent years. Consequently, there exist successful live virus vaccines for MDV which are logical candidates as source materials for developing a suitable vector. The MDV's are typically characterized by a double stranded DNA genome of approximately 150 to 180 kb and are classified as gamma-herpesviruses.

There are three distinct serotypes of MDV found in chickens: (1) serotype 1, an oncogenic virus which induces a T cell lymphoma in chickens and includes high- and low-virulent MDV and their attenuated variants; (2) serotype 2, a nononcogenic MDV; and (3) serotype 3, herpesvirus of turkeys (HVT). Neoplasms (lymphomas) induced by serotype 1 MDV can be prevented by vaccination with live virus preparations of serotype 2 and/or HVT. Although cross-reactive proteins have been detected, the three serotypes have unique DNA restriction patterns. The extent of DNA homology between the serotypes has been reported from as low as 5% to approaching 70%.

One difficulty in using MDV as a possible expression vector has been the failure so far to identify sequences which do not appear to be essential for replication of MDV as sites for the insertion of foreign genes. The thymidine kinase (tk) gene which has been used in other herpesviruses as an insertion site has not been identified in MDV. Screening for other sites is confounded by the absence of a positive selection system and the potential for lack of stability in regard to insertion and expression of any DNA. Also, there is a lack of basic knowledge of MDV, particularly with respect to promoters and transcriptional regulation.

2. Description of the Prior Art

Defective virus particles are often seen as a result of serial undiluted passage (high multiplicity of infection) of virus stocks of many types of viruses. Many herpesviruses have been observed to contain defective particles after serial propagation in vitro. N. Frenkel [Defective Interfering Herpesviruses, In The Human Herpesviruses—An Interdisciplinary Prospective (eds. A. J. Nahmias, W. R. Dowdle, and R. S. Schinazy), pp. 91–120, Elsevier-North Holland, Inc., New York, (1981)] has reported on two classes of defective viruses which contain different origins of replication in herpes simplex virus (HSV) stocks. These defective viruses have been shown to be head-to-tail reiterations (repeat units) of specific HSV DNA sequences (seed) which are amplified to form concatemers of approximately the full length of wild type virus [150 kilobases (kb)] and repackaged as defective particles [Spaete et al., Cell 30: 295–304 (1982)]. These defectives, termed amplicons, have been shown to carry cis-acting signals, an origin of replication and a packaging signal. The origin of replication and packaging signal allow replication and encapsidation of the defective particle when trans-acting functions are provided by a competent helper virus [Spaete et al., Proc. Natl. Acad. Sci. USA 82: 694–698 (1985); Vlazny et al., Proc. Natl. Acad. Sci. USA 78: 742–746 (1981)].

Yates et al. [Nature 313: 812–815 (1985)] reported a stable plasmid consisting of the ori P and EBNA-1 of Epstein-Barr virus with a selectable gene which persists at 1–3 copies/cell. This replicon is persistent and stable with serial passage (Yates et al. supra).

Amplicons have been shown to replicate and express foreign DNA sequences which have been engineered into the seed. Frenkel et al. [Eukaryotic Viral Vectors (ed. Y. Gluzman), Cold Spring Harbor (1982)] and Spaete et al. [Cell 30: 295–304 (1982)] reported on the construction of a chimeric amplicon by cloning a 3- to 8-kb repeat unit from HSV-1 defective genomes into a derivative of a bacterial plasmid. Cotransfection of cells with the amplicon and a helper virus resulted in the regeneration of chimeric defective genomes containing multiple reiterations of the seed DNA sequences containing repeat units in which the bacterial plasmid sequences were linked to the amplicon sequences. These chimeric defective genomes were efficiently packaged into structural virions and were structurally stable through multiple serial passaging in eucaryotic cell culture. The results established that foreign DNA sequences can be introduced into defective HSV genome repeat units and be stably propagated in virus populations when a helper virus is present.

Kwong et al. [J. Virol. 51(3): 595-603 (Sept. 1984)] has shown propagation of relatively large sets of eucaryotic DNA sequences within chimeric packaged defective genomes. The largest chimeric genomes tested having an overall size of 19.8 kb comprised a 12-kb DNA sequence encoding the chicken ovalbumin gene, an HSV repeat unit, and bacterial plasmid sequences. These genomes replicated in serial passage but were not as stable as other seed amplicons tested ranging in size from 11 to 15 kb and containing subsets of the 12-kb chicken DNA sequences.

It was later established by Kwong et al. [Virology 142: 421-425 (1985)] that a eucaryotic gene inserted into defective virus genomes could be expressed in HSV-infected cells. Sequences of the chicken ovalbumin gene were fused to an HSV alpha promoter and to genomic ovalbumin 3'-flanking sequences. The chimeric alpha-ovalbumin gene was introduced into defective HSV genomes which were stably propagated in serially passaged virus stocks in the presence of helper virus. The chimeric gene was abundantly expressed in cells infected with the resultant virus stocks.

SUMMARY OF THE INVENTION

We have now discovered a fragment of DNA (seed) in a defective Marek's disease virus which possesses the characteristics of an amplicon. When cotransfected into cell culture along with a parental helper virus, this seed will replicate and be amplified. The resulting defective virus can be serially passaged with the helper. Foreign DNA (genes) placed within the seed is also replicated [expressed] and stably maintained. This seed can be engineered to contain appropriate DNA and regulatory signals for expression of immunogenic proteins and could function as a vaccine or delivery vector. We have also discovered that genes or other DNA sequences associated with the seed will be inserted into the genome of the helper virus, which will then become the vehicle for expression.

In accordance with this discovery, it is an object of the invention to provide a vector for use in the development of avian vaccines or delivery of genes into the avian system.

A specific object of the invention is to develop from an avian herpesvirus amplicon a vector which can be engineered as either a monovalent or multivalent vaccine against avian diseases.

Another specific object of the invention is to develop from an avian herpesvirus a eucaryotic expression vector which is useful in the delivery of economically important genes to commercial poultry lines.

A further object of the invention is to employ a novel avian herpesvirus amplicon to insert foreign genes into a nondefective helper virus which will thereby become a eucaryotic expression vector for the foreign genes.

Other objects and advantages of this invention will become readily apparent from the ensuing description.

Glossary

For purposes of this invention, the following abbreviations and terms used herein have been defined below.

Abbreviations

AHV = avian herpesvirus
ALV = avian leukosis virus (exogenous oncogenic virus)
C/AB = chicken cells resistant to infection by subgroup A and B avian retroviruses
CEF = chicken embryo fibroblast
HVT = herpesvirus of turkeys (serotype 3, Marek's disease herpesvirus)
HP = high passage
HSV = herpes simplex virus
kb = kilobases (1000 base pairs)
LP = low passage
MDV = Marek's disease herpesvirus (an avian herpesvirus)
MP = medium passage

Terms amplicon: a fragment of viral DNA which contains all cis-acting functions required for DNA replication. In the presence of helper virus the amplicon infects host cells and replicates forming high molecular weight concatemers of DNA clone: in reference to DNA, the product or process of isolating a segment of DNA, linking it to a vector, and introducing it into a host for expansion concatemer: a head-to-tail repeat of a DNA or RNA fragment expression: the transcription of a gene into messenger RNA (mRNA) and the subsequent translation of the mRNA into a protein coded by the gene expression vector: a DNA sequence such as an amplicon or plasmid which is able to replicate in a host cell and express genes present in the DNA sequence foreign gene: a gene not normally characteristic of a particular genome, cell, or vector gene of interest: a gene, usually a foreign gene, which is desired to be inserted into a genome, cell, or vector infection: the introduction of bacteria or virus into cells or into a living organism wherein the bacteria or virus can replicate pA5: a plasmid comprising pUC18 ligated at the EcoRI site to the 4-kb amplicon pBR322: a standard plasmid cloning vector pUC18: a standard plasmid cloning vector replicon: DNA that can replicate autonomously in either procaryotes or eucaryotes subclone: in reference to DNA, the product or process of cloning a portion of an already cloned DNA segment transfection: acquisition of new genetic material in a cell by incorporation of added DNA such as a foreign gene transform: to change the characteristics of a host cell in response to DNA foreign to that cell vector: a derivative of a virus or plasmid constructed by recombinant DNA techniques and having a cloning site for inserting a gene of interest

| Restriction Enzyme | Cleavage Site |
|---|---|
| ApaI |  GGGCCC |
| BstEII |  GGTNACC |
| BglI |  GCCNNNNNGGC |

-continued

| Restriction Enzyme | Cleavage Site |
| --- | --- |
| EcoRI | ↓<br>GAATTC |
| HindIII | ↓<br>AAGCTT |
| KpnI | ↓<br>GGTACC |
| NdeI | ↓<br>CATATG |

DETAILED DESCRIPTION OF THE INVENTION

Figure 1:
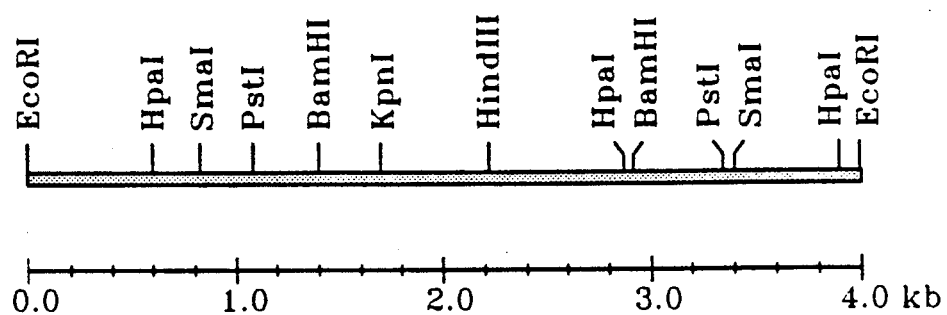
FIG. 1 is a restriction enzyme map of the 4 kb amplicon of the invention.
Figure 2:
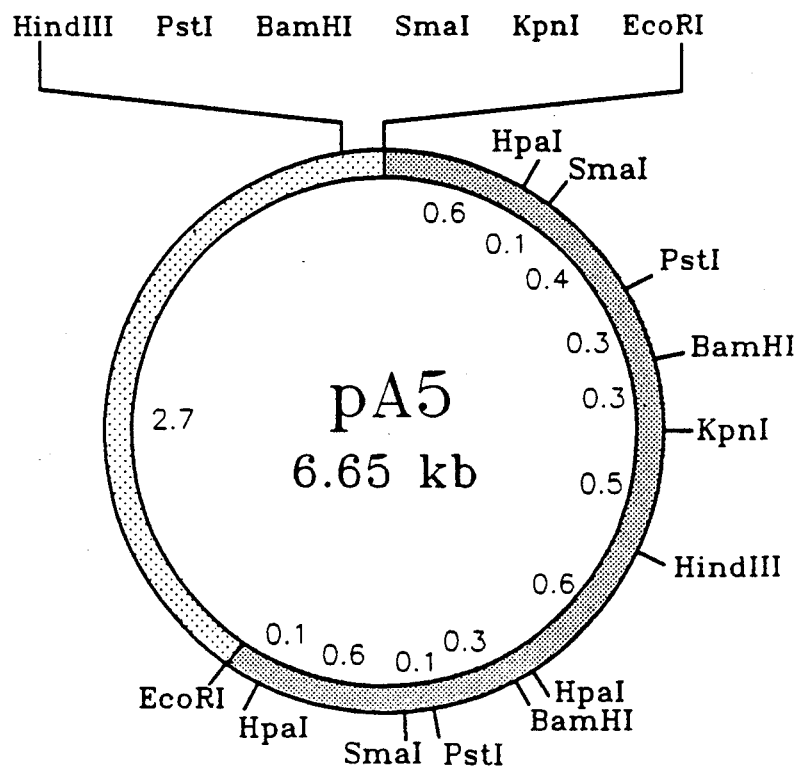
FIG. 2 is a restriction enzyme map of the plasmid pA5 comprising pUC18, a polylinker, and the amplicon of FIG. 1.

The DNA seed, or amplicon, constituting the subject of this invention is derived from MDV as previously mentioned. The particular source strain of MDV, from which the first such amplicon within the scope of this invention was derived, was an MDV serotype 2 field isolate designated 281 MI/1 and reported by Witter [Avian Dis. 27: 113-132 (1983). We have discovered that upon high serial passage (greater than about 58 passages) of strain 281 MI/1 on a suitable culture medium, there occurs significant alterations in restriction enzyme patterns of the DNA. One such alteration is indicative of the development of a defective form of the virus, comprising concatemeric reiterations of a segment (seed) of the viral DNA having a size of approximately 4 kb. This segment will hereafter be termed the "amplicon." A detailed description of the generation and isolation of the amplicon from the 281 MI/1 virus is given in Example 1.

Other MDV serotype 2 strains including SB-1, 287 C/1, and 298 B/1 have been subjected to the same serial passaging and restriction enzyme analyses as 281 MI/1. An amplicon-like fragment was detected in the 298 B/1 high passage virus, suggesting that this strain has also generated an amplicon. The implication of our observations is that the generation of an amplicon by MDV strains is an infrequent, but repeatable, event. However, we would hypothesize from the inherent genomic similarity that amplicons could eventually be isolated from most, if not all, MDV strains. A suitable passage medium for generating the amplicons would be chick embryo fibroblast (CEF). Our experience with the 281 MI/1 strain would indicate that at least 55 serial passages at a high multiplicity of infection would be required to generate defective viruses comprising the amplicons.

While the 4-kb amplicon isolated from the 281 MI/1 strain has not been sequenced, it is believed from hybridization studies to be a recombinant of various sequences present in the parental virus genome. Though the seed does contain the appropriate sequences necessary to initiate replication, the genome comprising the concatonated amplicons is defective in that it is incapable of infection or replication in the absence of a helper virus. Essential trans-components must be supplied by the nondefective helper virus. The helper may be the nondefective parent virus or any other infectious virus which encodes the necessary functions that can be provided in trans. Without necessarily being limited thereto, exemplary components encoded by the helper include appropriate polymerases required for replication and for the structural proteins needed for encapsidation. Examples of these, without limitation thereto, are those mentioned previously.

The utility of the invention arises from associating the amplicon with one or more genes of interest by ordinary recombinant techniques, and then amplifying the gene(s) by culture of the recombinant fragment in a suitable medium. This step of course would have to be in the presence of a helper virus for the reasons previously discussed. The culture product would then be used as a live recombinant DNA (rDNA) vaccine for the in vivo expression of the inserted gene(s) in somatic cells of inoculated birds. Alternatively, the genes can be expressed in vitro in somatic cell culture, and the expression products recovered from the medium.

We have also discovered that in cell culture, the amplicon has a tendency to insert foreign genes associated with it into the genome of the nondefective helper virus. In this manner, the amplicon functions as a transfer vector and is thereby useful in promoting the insertion of a gene of interest into an infectious form of the virus. The same helper viruses identified above could be modified in this manner for use as in vivo or in vitro expression vectors.

The genes of interest would include those which encode for immunogenic proteins and for beneficial economic traits desired in commercial lines. For example, expression of a gene coding for a retrovirus viral envelope antigen in the cell membrane of a fowl would interfere with infection by the viral subgroup defined by that particular envelope protein. Also, genes coding for various growth hormones or other regulatory functions related to fertility or meat production would be likely candidates for amplification and expression in accordance with the invention.

It is known from the published work with HSV amplicons discussed previously that the maximum fragment size which will stably concatonate is about 15 kb. Larger fragments are susceptible to random deletions of base sequences. Assuming the MDV amplicons are analogous to the HSV model, the gene(s) combined with the 4-kb seed are therefore limited to total maximum size of about 11 kb. This size is sufficient to permit the incorporation of a great variety of genes or gene combinations into the vector and allow for the construction of recombinant, multivalent vaccines. Also based upon the HSV model, it appears that the maximum length of the concatemer is about 150 kb. Thus, the number of individual gene replications in a concatameric unit is an inverse function of the total unit size.

The site chosen for insertion of the gene(s) within the amplicon is optional, provided that there is no interference with the replicative functions. The EcoRI site has been found to be nonessential to replication, and is therefore preferred for gene insertion.

The following examples are intended only to further illustrate the invention and are not intended to limit the scope of the invention which is defined by the claims.

EXAMPLE 1

Four serotype 2 strains (SB-1, 281 MI/1, 287 C/1, and 298 B/1) at low and high passage levels and three HVT strains (FC126, AC-16, and WTHV-1) at low passage levels were obtained from the Agricultural Research Service Regional Poultry Laboratory in East Lansing, Mich. The passage level refers to the number of in vitro passages after isolation with low passage (LP) <20, medium passage (MP) 20–60, and high passage (HP) >60. All strains were originally isolated from the field, cloned by plaque-purification before 20 passages, and serially passaged on CEF cultures at a high multiplicity of infection. The CEF cultures were prepared as described by Silva et al. [Virology 136: 307-320 (1984)]. High multiplicity of infection indicates passage at 2:1 to 4:1 of uninfected:infected cells. All isolates were passed on C/AB cells to restrict possible avian leukosis virus (ALV) contamination. Later, in vitro passage was on line 0 CEF which contain no endogenous ALV. Serial passage continued for at least 70 passages.

To determine if alterations in the restriction endonuclease pattern occur after serial in vitro passage, total DNA was isolated from virus-infected CEF. Cells were infected at a high multiplicity of infection and maintained until extensive cytopathic effect was evident. Cells were scraped into the media, pelleted, washed once with phosphate-buffered saline and incubated for 4 to 24 hours at 39° C. in 10 volumes of NES-proteinase K solution (0.15M NaCl, 0.1M EDTA, 1% sodium dodecyl sulfate, proteinase K at 100 micrograms per ml.). The DNA was extracted twice with an equal volume of phenol-chloroform-isoamyl alcohol (25:24:1) and twice with chloroform-isoamyl alcohol (24:1) before precipitation with ethanol. Isolated DNA was resuspended in TE (10 mM Tris, pH 8.0, and 1 mM EDTA) for further characterization and use.

To determine restriction endonuclease fragment patterns, three different restriction endonucleases (BamHI, BglI, and EcoRI) were used to examine DNA from infected cells at various passage levels. DNA from serotype 2 infected cells was examined at the 17th passage, at the 58th passage, and at the 93rd passage. DNA from HVT infected cells was examined at LP and at 10 passage intervals through 70 passages. Digested DNA was examined by 0.6% agarose gel electrophoreses in TBE (89 mM Tris, 89 mM boric acid, 2 mM EDTA). Sizes of RE-generated fragments were determined by coelectrophoresis with an EcoRI plus HindIII or a BstEII digest of lambda-phage DNA and interpolation. All digests resulted in strain variation in discrete bands. The EcoRI and BamHI digests showed the greatest strain variation. EcoRI digestion resulted in unique bands for each strain at 2.9 to 3.5 kb with strain 298 B/1 having the greatest variation. With BamHI digestion, unique bands for each strain were seen at 4.5 to 4.9 kb and 2.6 to 2.8 kb.

All HVT strains showed both strain variation and passage variation by 40 passages with all restriction endonucleases used. The variations seen between strains with EcoRI and BamHI digestion could be distinguished only in the LP DNA. The strain specific band consistently disappeared with passage. A single band from LP DNA disappeared by 60 serial passages. This band was 7.9–8.4 kb for EcoRI digestion, 10.5–10.6 kb for BamHI digestion, and 9.6–9.9 kb for BglI digestion.

All four strains of serotype 2 showed variation in fragment patterns after serial passage and digestion with the three enzymes except BamHI digest of 287 C/1 and BglI digest of 281 MI/1 and 298 B/1. The alterations consisted of the loss of a band(s) at LP and/or appearance of new DNA band(s) at HP. The most striking change was seen with strain 281 MI/1 as shown in Table I below. At HP in both the EcoRI and BamHI digests, new bands of greater than molar intensity were found. These bands were at about 4 kb (3.8 kb) in the EcoRI digest and approximately 2.4 and 1.6 kb in the BamHI digest.

To determine the origin of the amplified bands, the DNA was probed under high stringency conditions. For high stringency hybridization, the DNA was electrotransferred to "Zeta-Probe" or "Nytran" nylon membrane. The agarose gels for electrotransfer were soaked for 30 minutes in 0.2M NaOH–0.5M NaCl and neutralized by soaking three times (10 minutes each) in TAE buffer [20 mM sodium acetate, 1 mM EDTA, 40 mM Tris base (pH 7.4)].

TABLE I

Alterations in Restriction Digest Patterns for Strain 281 MI/1 After Serial Passage In Vitro

| Restriction Enzyme | | | | | |
|---|---|---|---|---|---|
| EcoRI | | BglI | | BamHI | |
| LP[a] | HP[b] | LP | HP | LP | HP |
| — | — | 6.4 | 6.4 | — | — |
| — | 5.5 | — | — | — | — |
| 5.1 | — | — | — | — | — |
| — | — | — | — | 4.75 | 4.75 |
| — | — | 4.5 | 4.5 | 4.5 | 4.5 |
| — | — | — | — | — | 4.4 |
| — | — | — | 4.1 | — | — |
| — | 4.0[c] | — | — | — | — |
| — | 3.6 | — | — | — | — |
| 3.1 | 3.1 | — | — | — | — |
| — | — | 2.9 | 2.9 | — | — |
| — | 2.7 | — | — | — | — |
| 2.65 | — | — | — | — | — |
| — | — | — | — | 2.6 | 2.6 |
| — | — | — | — | — | 2.4[c] |
| — | — | — | 1.9 | — | — |
| — | — | — | — | — | 1.6[c] |

[a]Low passage DNA fragments (in kilobases).
[b]High passage DNA fragments (in kilobases).
[c]Fragments present in much greater than molar quantities.

The transfer was in a "Bio-Rad Trans-Blot" system at 4° C. with TAE buffer at 20 V. for 30 minutes followed by 30 V. for 3 hours. The membranes were washed briefly in TAE buffer, dried, and baked for 2 hours at 80° C. $^{32}P$-probes were prepared by standard nick translation procedures with [alpha-$^{32}P$]-dCTP. Hybridization conditions were carried out at a stringency greater than 95% (high stringency 0.1 x SSC wash at 65° C.). After washing, filters were dried and exposed to X-ray film (Kodak "X-Omat AR") with intensifying screens (Kodak "X-Omatic") at −70°.

The amplified bands were shown to be from viral origin as only DNA from virus-infected cells hybridized to the isolated 4-kb band. The 4-kb band probe indicated several differences between low and high passage DNA which was not evident by ethidium bromide staining. The HP isolate from 298 B/1 had several high molecular weight bands not present in the LP isolates.

High and low passage DNA was digested with XmnI, BglII, PvuII, and XbaI. These enzymes do not cut within the amplified band. The digested DNA was transferred to nylon and probed with isolated amplified DNA. HP DNA contained high molecular weight DNA which was greater than 20 kb in size and was not present in LP DNA.

Cloning Viral DNA into pUC18

In order to characterize the amplified 4-kb EcoRI fragment, total DNA isolated from cells infected with 281 MI/1 HP was digested with EcoRI and inserted into the EcoRI site of pUC18 with T4 DNA ligase [Maniatis et al., Molecular Cloning: A Laboratory Manual, Cold Spring Harbor Laboratory, Cold Spring Harbor, N.Y. (1982)]. The ligated DNA was used to transform strain JM109 E. coli following the protocol described by Hanahan [J. Mol. Biol. 166: 557–580 (1983)]. When plated on LB plates containing ampicillin, X-gal, and IPTG, 141 ampicillin-resistant white colonies were selected. These colonies were grown overnight and the DNA extracted for examination. Of the 141 colonies, 24 (17%) contained an insert of 3.7–4.3 kb. At least 14 (9.9%) colonies were identified as homologous to the amplified DNA in 281 MI/1 HP. Mini preparations of plasmid DNA were prepared by alkaline lysis (Maniatis et al., supra) and screened for the presence of inserts by digestion with EcoRI and subsequent agarose gel electrophoresis. Clones containing the appropriately sized insert (3.6–4.3 kb) were further examined by restriction enzyme analysis. Final identification of the clones containing the appropriate DNA was by nick translation of recombinant plasmid DNA and hybridization to EcoRI digested, total DNA from HP-virus infected cells. When the identified plasmid (pA5) or the 4-kb fragment isolated from total HP-infected cell DNA was used to probe 281 MI/1 DNA, the resulting autoradiographs were virtually identical.

Restriction mapping of the identified plasmid (pA5) was by double digestion with various restriction endonucleases. A single restriction site within the insert was found for HindIII, KpnI, ApaI, and NdeI. BamHI had two sites within the 4-kb insert. The preliminary restriction map shown in FIG. 1 is in agreement with the data from total HP-viral DNA digestion.

EXAMPLE 2

To investigate the possibility that the 4-kb fragment identified and characterized in Example 1 could function as an amplicon or vector, it was important to determine if a competent helper virus would allow the fragment to replicate and amplify. It was also considered necessary to identify any restriction endonuclease sites within the 4-kb fragment which might serve as possible insertion sites.

Accordingly, the 4-kb fragment was cotransfected with total infected cell DNA as a helper into line 0 CEF. Both 281 MI/1 MP and FC126 were tested as helpers, as neither contains the amplified 4-kb fragment. The cloned DNA was employed in several different forms: (1) total pA5 DNA; (2) linear viral DNA isolated from pA5 after EcoRI digestion; (3) the viral DNA of (2) ligated to form circles; and (4) the ligated DNA of (3) digested and relinearized with (a) HindIII, (b) KpnI, (c) ApaI, or (d) NdeI. The total pA5 was used to determine if foreign DNA ligated to the seed would be replicated and transmitted. The circularized DNA was employed to protect against inadvertent cutting at a site which was necessary for replication of the seed. Digestion after ligation with the various restriction enzymes having single sites in the seed was carried out to determine which areas of the DNA were essential for successful cotransfection.

In each experiment, 50 ng. of cloned DNA was coprecipitated with 2 micrograms of helper virus DNA, resuspended in water, and used to transfect one 60-mm. plate of secondary CEF. The protocol for transfection was that described by Kawai et al. [Mol. Cell. Biol. 4: 1172–1174 (1984)]. Briefly, secondary CEF were plated at $8 \times 10^5$ cells/60-mm. dish 18 hours before use. Cells were fed with fresh media containing 4% calf serum 2 hours before transfection. Polybrene was added to the cultures at the level of 30 micrograms/ml. followed by the DNA. Cultures were incubated at 37° C. for 6 hours, shocked with 30% DMSO for 4 minutes, and fed with media containing 4% calf serum. Cultures were observed for the appearance of cytopathic effects, at which time they were overlaid with agar, individual foci were selected, and infected cells transferred to a fresh monolayer of CEF. At passage 2 to 8, DNA was isolated, digested with EcoRI, and examined for the presence of the transfected DNA. Determination of the molarity of the bands present was by micro-densitometer scanning of photographic negatives from ethidium bromide stained agarose gels.

281 MI/1 MP did function as a helper virus while FC126 did not. Of 13 isolated foci which received 281 MI/1 MP and ligated seed, 11 were positive for the appearance of a 4-kb band. Zero of six isolated DNA samples which were transfected with 281 MI/1 MP only and zero of 15 samples cotransfected with seed plus FC126 helper virus DNA showed the appearance of a 4-kb band. Seed which had been cut with EcoRI was the only linear seed which resulted in the replication of the 4-kb band, indicating the necessity of intact DNA in the regions of the other restriction enzymes. Cotransfection with the total plasmid, pA5, resulted in detectable DNA from both the seed and pUC18. The results are summarized in Table II, below.

EXAMPLE 3

To determine the stability of the cotransfected isolates from Example 2, viral stocks which had been stored at $-196°$ C. following the cotransfection experiments were passaged on CEF monolayers at approximately 1:4 (infected:uninfected cells) and infected cells were serially passaged at a similar level through eight passages. DNA was isolated from infected cells and digested with EcoRI before analysis by agarose gel electrophoresis. The results show the 4-kb band or other alterations remained stable with serial passage. The 4-kb band was amplified in all positive isolates by six to eight passages. pUC18 DNA was present in one isolate (A5-1) and showed some amplification; however, the level of amplification of pUC18 DNA was less than the amplification seen with the seed DNA.

EXAMPLE 4

In vivo studies were performed to determine if a defective virus containing foreign DNA would replicate in birds. One-day-old birds were inoculated with $10^4$ plaque-forming units of helper virus only or helper virus plus defective.

TABLE II

| | Amplicon Replication | |
|---|---|---|
| DNA | RE Digestion of input amplicon | Presence of amplicon |
| 281 MI/1 & amplicon[a] | EcoRI | +[b] |
| 281 MI/1 | none | − |
| FC126 & amplicon | EcoRI | − |
| 281 MI/1 & amplicon | KpnI | − |
| 281 MI/1 & amplicon | HindIII | − |
| 281 MI/1 & pA5 | none | + |
| 281 MI/1 & pA5 | EcoRI | + |

[a]The amplicon of pA5 was digested with the appropriate RE enzyme. The resulting DNA was mixed with DNA from either 281 MI/1 or FC126 and cotransfected into CEF.
[b]A "+" indicates that an amplified 4 kb DNA fragment was detected in an EcoRI digest of total DNA from infected cells.

At 12 days, blood was collected for virus isolation. The DNA from the isolated virus was examined for the presence of the foreign DNA. The results showed that DNA from virus isolated from 7 of 11 birds receiving helper plus defective, and zero of 13 receiving helper only, contained foreign DNA sequences. This indicates that the defective virus successfully delivers foreign DNA which is replicated during virus infection in the bird. The potential for expressing foreign genes has been shown by the development of a vector delivery system.

Restriction endonuclease digestion analysis indicated that, in some cases, the foreign DNA is recombined back into the helper virus genome to give rise to a nondefective recombinant virus. Therefore, in addition to amplifying the foreign DNA, the 4-kb defective virus also functions as a shuttle vector to transfer foreign DNA into the helper-virus genome. This suggests that a second use for the 4-kb amplicon is as a vector to create nondefective live recombinant vaccines.

EXAMPLE 5

This experiment was designed to demonstrate expression in vitro of a foreign eucaryotic gene amplified by means of the amplicon described above in Example 1. The gene was for a bovine growth hormone, and it was obtained as a construct in a plasmid with a cytomegalovirus promoter. This construct in turn was ligated into a plasmid (PJCI-BGH) which contained the amplicon "seed" (pA5) and was cotransfected into fibroblast cells with helper virus. An isolate was identified which contained the amplicon, thereby indicating that the amplicon seed can accommodate greater than 6 kb of foreign DNA and be stably replicated in vitro. However, there was no evidence of expression of the bovine growth hormone.

It is understood that the foregoing detailed description is given merely by way of illustration and that modification and variations may be made therein without departing from the spirit and scope of the invention.

We claim:

1. A substantially biologically pure amplicon derived from a Marek's disease virus as a DNA fragment thereof, wherein said amplicon contains all cis-acting functions required for DNA replication, and in the presence of helper virus, said amplicon infects host cells and replicates, thereby forming high molecular weight concatemers of DNA.

2. The amplicon of claim 1 characterized by a length of about 4 kilobases.

3. The amplicon of claim 1 characterized by a length of about 4 kilobases and having a restriction enzyme map as shown in FIG. 1.

4. An amplicon as described in claim 1 wherein said Marek's disease virus is strain 281 MI/1.

5. Recombinant DNA comprising a substantially biologically pure amplicon derived from a Marek's disease virus and a foreign DNA sequence derived from a source other than said Marek's disease virus, wherein said amplicon contains all cis-acting functions required for DNA replication, and in the presence of helper virus, said amplicon infects host cells and replicates, thereby forming high molecular weight concatemers of DNA.

6. The DNA of claim 5 wherein said amplicon is characterized by a length of about 4 kilobases.

7. The DNA of claim 5 wherein said amplicon is characterized by a length of about 4 kilobases and a restriction enzyme map as shown in FIG. 1.

8. The DNA of claim 7 wherein said foreign DNA sequence is a cloning plasmid.

9. The DNA of claim 5 wherein said foreign DNA sequence is an avian gene capable of being amplified concurrent with formation of concatemers by said amplicon.

10. A method for amplifying a foreign gene comprising transfecting cells in the presence of a helper virus with a recombinant DNA vector comprising a substantially biologically pure amplicon derived from a Marek's disease virus and said foreign gene, wherein said amplicon contains all cis-acting functions required for DNA replication, and in the presence of helper virus, said amplicon infects host cells and replicates, thereby forming high molecular weight concatemers of DNA.

11. The method of claim 10 wherein said amplicon is characterized by a length of about 4 kilobases and a restriction enzyme map as shown in FIG. 1.

12. The method of claim 11 wherein said Marek's disease virus is strain 281 MI/1.

* * * * *